US009597129B2

(12) United States Patent
Keller et al.

(10) Patent No.: US 9,597,129 B2
(45) Date of Patent: Mar. 21, 2017

(54) REINFORCED INTRAMEDULLARY NAIL (75) Inventors: Samuel Keller, Hettingen (CH);
Jordan Velikov, Thalwil (CH); Reto Senger, Winterthur (CH)

(73) Assignee: Zimmer GmbH, Winterthur (CH)

( * ) Notice: Subject to any disclaimer, the term of this patent is extended or adjusted under 35 U.S.C. 154(b) by 739 days.

(21) Appl. No.: 12/601,680

(22) PCT Filed: May 23, 2008

(86) PCT No.: PCT/US2008/064680
§ 371 (c)(1),
(2), (4) Date: Jan. 20, 2010

(87) PCT Pub. No.: WO2008/147975
PCT Pub. Date: Dec. 4, 2008

(65) Prior Publication Data
US 2010/0179551 A1    Jul. 15, 2010

Related U.S. Application Data (60) Provisional application No. 60/931,783, filed on May 25, 2007.

(51) Int. Cl.
*A61B 17/74* (2006.01)
*A61B 17/72* (2006.01)

(52) U.S. Cl.
CPC ........ *A61B 17/744* (2013.01); *A61B 17/7283* (2013.01); *A61B 17/7258* (2013.01); *A61B 17/7291* (2013.01)

(58) Field of Classification Search
CPC ............ A61B 17/7258; A61B 17/7283; A61B 17/744; A61B 17/72; A61B 17/846; A61B 17/74
USPC ...................................... 606/62–68
See application file for complete search history.

(56) References Cited

U.S. PATENT DOCUMENTS

| 2,239,088 A | 4/1941 | Ettinger |
| 2,518,019 A | 8/1950 | Kane |
| 3,433,220 A | 3/1969 | Zickel |
| 4,103,683 A | 8/1978 | Neufeld |

(Continued)

FOREIGN PATENT DOCUMENTS

| CN | 2471292 Y | 1/2002 |
| DE | 4318150 A1 | 12/1994 |

(Continued)

OTHER PUBLICATIONS

The Published International Application No. PCT/US2008/064680 as WO2008/147975A1 with the International Search Report.
The International Preliminary Report on Patentability mailed Dec. 1, 2009 in related International Application No. PCT/US2008/064680.
The Written Opinion and International Search Report mailed 1/1/26/10 in related International Application No. PCT/EP2009/007353.

(Continued)

*Primary Examiner* — Jan Christopher Merene
*Assistant Examiner* — Atiya Mahmud
(74) *Attorney, Agent, or Firm* — Schwegman Lundberg & Woessner, P.A.

(57) ABSTRACT

An orthopedic implant assembly is disclosed for the treatment of fracture or other trauma to a long bone. The implant assembly includes an intramedullary nail and a lag screw that extends through a transverse bore of the intramedullary nail. The intramedullary nail includes an elongated body and one or more enlarged portions positioned adjacent to the transverse bore to reinforce the intramedullary nail.

16 Claims, 7 Drawing Sheets

(56) References Cited

U.S. PATENT DOCUMENTS

| | | | |
|---|---|---|---|
| 4,446,857 A | 5/1984 | Otte et al. | |
| D279,502 S | 7/1985 | Halloran | |
| D279,503 S | 7/1985 | Halloran | |
| 4,622,959 A | 11/1986 | Marcus | |
| 4,697,585 A | 10/1987 | Williams | |
| 4,776,330 A | 10/1988 | Chapman et al. | |
| 4,805,607 A | 2/1989 | Engelhardt et al. | |
| 4,817,591 A | 4/1989 | Klaue | |
| 4,827,917 A | 5/1989 | Brumfield | |
| 4,846,162 A | 7/1989 | Moehring | |
| 4,875,474 A | 10/1989 | Border | |
| 4,875,475 A | 10/1989 | Comte et al. | |
| 4,895,572 A | 1/1990 | Chernoff | |
| 4,976,258 A | 12/1990 | Richter et al. | |
| 4,981,481 A | 1/1991 | Kranz | |
| 5,032,125 A | 7/1991 | Durham et al. | |
| 5,034,013 A | 7/1991 | Kyle et al. | |
| 5,035,697 A | 7/1991 | Frigg | |
| 5,041,114 A | 8/1991 | Chapman et al. | |
| 5,041,115 A | 8/1991 | Frigg et al. | |
| 5,057,103 A | 10/1991 | Davis | |
| 5,057,110 A | 10/1991 | Kranz et al. | |
| 5,112,333 A | 5/1992 | Fixel | |
| 5,116,335 A | 5/1992 | Hannon et al. | |
| 5,122,141 A | 6/1992 | Simpson et al. | |
| 5,167,663 A | 12/1992 | Brumfield | |
| 5,176,681 A | 1/1993 | Lawes et al. | |
| 5,201,735 A | 4/1993 | Chapman et al. | |
| 5,312,406 A | 5/1994 | Brumfield | |
| 5,356,410 A | 10/1994 | Pennig | |
| 5,397,328 A | 3/1995 | Behrens et al. | |
| 5,489,284 A | 2/1996 | James | |
| 5,499,986 A | 3/1996 | Dimarco | |
| 5,531,748 A | 7/1996 | de la Caffiniere | |
| 5,549,610 A | 8/1996 | Russell et al. | |
| 5,573,536 A | 11/1996 | Grosse et al. | |
| 5,578,035 A | 11/1996 | Lin | |
| 5,620,445 A | 4/1997 | Brosnahan et al. | |
| 5,643,258 A | 7/1997 | Robioneck et al. | |
| 5,653,709 A | 8/1997 | Frigg | |
| 5,658,287 A | 8/1997 | Hofmann et al. | |
| 5,658,288 A | 8/1997 | Kim | |
| 5,713,902 A | 2/1998 | Friedl | |
| 5,766,174 A | 6/1998 | Perry | |
| 6,010,506 A | 1/2000 | Gosney et al. | |
| 6,019,761 A | 2/2000 | Gustilo | |
| 6,022,352 A | 2/2000 | Vanderwalle | |
| 6,106,528 A | 8/2000 | Durham et al. | |
| 6,123,708 A * | 9/2000 | Kilpela | A61B 17/72 606/62 |
| 6,168,595 B1 | 1/2001 | Durham et al. | |
| 6,210,414 B1 | 4/2001 | Lin | |
| 6,221,074 B1 | 4/2001 | Cole et al. | |
| 6,224,601 B1 * | 5/2001 | Friedl | 606/64 |
| 6,231,576 B1 | 5/2001 | Frigg et al. | |
| 6,235,031 B1 | 5/2001 | Hodgeman et al. | |
| 6,261,290 B1 | 7/2001 | Friedl | |
| 6,270,499 B1 | 8/2001 | Leu et al. | |
| 6,296,645 B1 | 10/2001 | Hover | |
| 6,319,253 B1 | 11/2001 | Ackeret et al. | |
| 6,402,753 B1 | 6/2002 | Cole et al. | |
| 6,406,477 B1 | 6/2002 | Fujiwara | |
| 6,443,954 B1 | 9/2002 | Bramlet et al. | |
| 6,488,684 B2 | 12/2002 | Bramlet et al. | |
| 6,524,314 B1 * | 2/2003 | Dean et al. | 606/64 |
| 6,527,775 B1 | 3/2003 | Warburton | |
| 6,558,388 B1 | 5/2003 | Bartsch et al. | |
| 6,562,042 B2 | 5/2003 | Nelson | |
| 6,569,165 B2 | 5/2003 | Wahl et al. | |
| 6,648,889 B2 | 11/2003 | Bramlet et al. | |
| 6,706,046 B2 | 3/2004 | Orbay et al. | |
| 6,783,530 B1 | 8/2004 | Levy | |
| 6,786,908 B2 | 9/2004 | Hover et al. | |
| 6,808,527 B2 | 10/2004 | Lower et al. | |
| 6,835,197 B2 | 12/2004 | Roth et al. | |
| 6,855,146 B2 | 2/2005 | Frigg et al. | |
| 6,921,400 B2 | 7/2005 | Sohngen | |
| 6,926,719 B2 | 8/2005 | Sohngen et al. | |
| 6,932,818 B2 | 8/2005 | Behrens | |
| 6,932,819 B2 | 8/2005 | Wahl et al. | |
| 6,981,976 B1 | 1/2006 | Schoenefeld | |
| 7,001,386 B2 | 2/2006 | Sohngen et al. | |
| 7,008,425 B2 | 3/2006 | Phillips | |
| 7,018,380 B2 | 3/2006 | Cole | |
| 7,041,104 B1 | 5/2006 | Cole et al. | |
| 7,135,023 B2 * | 11/2006 | Watkins | A61B 17/748 606/65 |
| 7,160,302 B2 | 1/2007 | Warburton | |
| 7,182,765 B2 | 2/2007 | Roth et al. | |
| 7,232,442 B2 | 6/2007 | Sohngen et al. | |
| 7,232,443 B2 | 6/2007 | Zander et al. | |
| 7,247,171 B2 | 7/2007 | Sotereanos | |
| 7,883,509 B2 | 2/2011 | Ferrante et al. | |
| 2001/0012939 A1 | 8/2001 | Wahl et al. | |
| 2001/0034523 A1 | 10/2001 | Nelson | |
| 2002/0029041 A1 | 3/2002 | Hover et al. | |
| 2002/0032445 A1 | 3/2002 | Fujiwara | |
| 2002/0103488 A1 | 8/2002 | Lower et al. | |
| 2002/0107578 A1 | 8/2002 | Speitling et al. | |
| 2002/0111629 A1 | 8/2002 | Phillips | |
| 2002/0133156 A1 | 9/2002 | Cole | |
| 2002/0151898 A1 | 10/2002 | Sohngen et al. | |
| 2002/0156473 A1 | 10/2002 | Bramlet et al. | |
| 2003/0004514 A1 * | 1/2003 | Frigg et al. | 606/62 |
| 2003/0018336 A1 * | 1/2003 | Vandewalle | A61B 17/72 606/67 |
| 2003/0069581 A1 | 4/2003 | Stinson et al. | |
| 2003/0074000 A1 | 4/2003 | Roth et al. | |
| 2003/0083661 A1 | 5/2003 | Orbay et al. | |
| 2003/0114855 A1 | 6/2003 | Wahl et al. | |
| 2003/0171819 A1 | 9/2003 | Sotereanos | |
| 2003/0195515 A1 | 10/2003 | Sohngen | |
| 2004/0010255 A1 | 1/2004 | Warburton | |
| 2004/0153073 A1 | 8/2004 | Orbay | |
| 2004/0158249 A1 | 8/2004 | Roth et al. | |
| 2004/0172027 A1 * | 9/2004 | Speitling et al. | 606/62 |
| 2004/0260290 A1 | 12/2004 | Zander et al. | |
| 2005/0010223 A1 * | 1/2005 | Gotfried | 606/62 |
| 2005/0055023 A1 | 3/2005 | Sohngen et al. | |
| 2005/0055024 A1 | 3/2005 | James et al. | |
| 2005/0065520 A1 | 3/2005 | Orbay | |
| 2005/0069397 A1 | 3/2005 | Shavit et al. | |
| 2005/0070903 A1 | 3/2005 | Roth et al. | |
| 2005/0075637 A1 | 4/2005 | Semet | |
| 2005/0080335 A1 | 4/2005 | Simon et al. | |
| 2005/0143739 A1 | 6/2005 | Shinjo et al. | |
| 2005/0149024 A1 | 7/2005 | Ferrante et al. | |
| 2005/0149025 A1 | 7/2005 | Ferrante et al. | |
| 2005/0159749 A1 | 7/2005 | Levy et al. | |
| 2005/0203510 A1 | 9/2005 | Sohngen | |
| 2005/0273103 A1 | 12/2005 | Wahl et al. | |
| 2005/0277936 A1 | 12/2005 | Siravo et al. | |
| 2005/0283154 A1 | 12/2005 | Orbay et al. | |
| 2006/0015101 A1 | 1/2006 | Warburton et al. | |
| 2006/0015123 A1 * | 1/2006 | Fencl | A61B 17/1659 606/104 |
| 2006/0069392 A1 | 3/2006 | Renzi Brivio et al. | |
| 2006/0084997 A1 | 4/2006 | Dejardin | |
| 2006/0084999 A1 | 4/2006 | Aschmann | |
| 2006/0095039 A1 * | 5/2006 | Mutchler | 606/64 |
| 2006/0100624 A1 | 5/2006 | Orbay et al. | |
| 2006/0106384 A1 | 5/2006 | Reber et al. | |
| 2006/0106389 A1 | 5/2006 | Reber et al. | |
| 2006/0111716 A1 | 5/2006 | Schlienger et al. | |
| 2006/0111717 A1 | 5/2006 | Saueressig et al. | |
| 2006/0122600 A1 | 6/2006 | Cole | |
| 2006/0142763 A1 | 6/2006 | Munro et al. | |
| 2006/0149247 A1 | 7/2006 | Frigg et al. | |
| 2006/0149248 A1 | 7/2006 | Schlienger et al. | |
| 2006/0149257 A1 | 7/2006 | Orbay et al. | |
| 2006/0161155 A1 | 7/2006 | Schlienger et al. | |
| 2006/0173457 A1 * | 8/2006 | Tornier | 606/62 |
| 2006/0189988 A1 | 8/2006 | Schlienger et al. | |
| 2006/0200142 A1 | 9/2006 | Sohngen et al. | |

(56) References Cited

U.S. PATENT DOCUMENTS

| | | | |
|---|---|---|---|
| 2006/0200143 | A1 | 9/2006 | Warburton |
| 2006/0200144 | A1 | 9/2006 | Warburton |
| 2006/0200160 | A1* | 9/2006 | Border .................. A61B 17/72 606/88 |
| 2006/0235394 | A1 | 10/2006 | Martin |
| 2006/0235395 | A1 | 10/2006 | Frigg et al. |
| 2006/0241604 | A1 | 10/2006 | Frigg et al. |
| 2006/0241605 | A1 | 10/2006 | Schlienger et al. |
| 2006/0264943 | A1 | 11/2006 | Chieng |
| 2006/0264944 | A1 | 11/2006 | Cole |
| 2007/0016203 | A1 | 1/2007 | Schlienger et al. |
| 2007/0049938 | A1 | 3/2007 | Wallace et al. |
| 2007/0049939 | A1 | 3/2007 | Wallace et al. |
| 2007/0049940 | A1 | 3/2007 | Wallace et al. |
| 2007/0100342 | A1 | 5/2007 | Green et al. |
| 2007/0100343 | A1 | 5/2007 | Cole et al. |
| 2007/0123876 | A1* | 5/2007 | Czartoski et al. ............. 606/62 |
| 2007/0270846 | A1* | 11/2007 | Metzinger ....................... 606/64 |
| 2008/0058814 | A1* | 3/2008 | Gotfried ......................... 606/62 |
| 2008/0249580 | A1 | 10/2008 | Evans |

FOREIGN PATENT DOCUMENTS

| | | |
|---|---|---|
| EP | 0257118 A1 | 3/1988 |
| EP | 0306709 B1 | 12/1992 |
| EP | 0517435 A1 | 12/1992 |
| EP | 1363545 A1 | 11/2003 |
| EP | 1452144 A2 | 9/2004 |
| EP | 1330988 B1 | 10/2004 |
| EP | 1522268 A1 | 4/2005 |
| FR | 2668360 A1 | 4/1992 |
| JP | 2295556 A | 12/1990 |
| JP | 5237136 A | 9/1993 |
| JP | 7222753 A | 8/1995 |
| JP | 2000-051224 A | 2/2000 |
| WO | WO99/20195 A1 | 4/1999 |
| WO | WO99/44528 A1 | 9/1999 |
| WO | WO00/15127 A1 | 3/2000 |
| WO | WO02/080790 A1 | 10/2002 |
| WO | WO03/030749 A1 | 4/2003 |
| WO | WO2004/002342 A2 | 1/2004 |
| WO | WO2005/122932 A2 | 12/2005 |
| WO | WO2006/019956 A2 | 2/2006 |
| WO | WO2006/105685 A2 | 10/2006 |
| WO | WO2007/009123 A2 | 1/2007 |
| WO | WO2007/023101 A1 | 3/2007 |
| WO | WO2008/147975 A1 | 12/2008 |

OTHER PUBLICATIONS

"Comparative Analysis of Interlocking Intramedullary Fracture Fixation Nails in Bending and Torsion" Bechtold et al., Resna 9th Annual Conference Paper, 1986, pp. 207-209.

"Comparison of the bone modeling effects caused by curved and straight nickel-titanium intramedullary nails" Kujala et al., Journal of Materials Science: Materials in Medicine, vol. 13, No. 12, 2002, pp. 1157-1161.

"Zickel Supracondylar Nail", R.E. Zickel, Techniques in Orthopaedics, vol. 9, No. 3, 1994, pp. 217-220.

"A Study on the Prebent Intramedullary Nails for the Femoral Fractures", Onoue, Journal of the Japanese Orthopaedic Association, 1977, pp. 315-329.

Proximal angle or continuous bend in unreamed intramedullary nailing: an experimental study, Langenbecks Archive for Surgery, vol. 382, No. 5, 1997, pp. 257-265.

"Preliminary clinical experience with a new fluted humeral nail" C. Garnavos, Injury, vol. 25, No. 4, 1994, pp. 241-245.

"Design and Clinical Application of Two Rectangle-Shaped Flexible Intramedullary Nails for Tibial Fracture" Yang et al., Zhonghua Wai Ke Za Zhi, vol. 25, No. 8, 1987, pp. 474-476, 502.

"Proximal Tibial Fracture Stability with Intramedullary Nail Fixation Using Oblique Interlocking Screws" Laflamme etal, Orthopaedic Trauma, vol. 17, No. 7, 2003, pp. 496-502.

"The use of the Hansen-Street intramedullary nail in midshaft fractures of the femur" Grimberg et al., Bulletin Hospital for Joint Diseases, vol. 53, No. 1, Spring 1993, pp. 45-50.

"Derby Intramedullary Nail—Further Biomechanical Comparison" Pratt et al., Journal of Biomedical Engineering, vol. 9, No. 1, 1987, pp. 84-87.

"Derby Intramedullary Nail—A Biomechanical Comparison" Papagiannopoulos et al., Journal of Biomedical Engineering, vol. 7, No. 4, 1985, pp. 313-317.

"Difficulty in removal of certain intramedullary nails" Seligson et al., Clinical Orthopaedics and Related Research, No. 340, 1997, pp. 202-206.

"Intramedullary Forearm Nailing", Dana M. Street, Clinical Orthopaedics and Related Research, No. 212, Nov. 1986, pp. 219-230.

"The AO/AsIF-proximal femoral nail (PFN): a new device for the treatment of unstable proximal femoral fractures" Simmermacher et al., Injury, vol. 30, No. 5, 1999, pp. 327-332.

"Two New Intramedullary Implant Designs for Phalanx Fixation in Digital Replantation: An Experimental Study" Kayikcioglu et al., Annals of Plastic Surgery, vol. 45, No. 3, 2000, pp. 258-263.

"The BEHAC nail—a new intramedullary implant for managing 2-stage fractures of the humerus" Alt et al., Unfallchirurg, vol. 105, No. 5, 2002, pp. 471-473.

"Initial Experience with a Second Genreation Locking Femoral Nail: The Russell-Taylor Reconstruction Nail" Hoover et al., Contemporary Orthopaedics, Sep. 1981, vol. 23, No. 3, pp. 199-208.

"Flexible intramedullary pins in the treatment of unstable proximal humeral fractures" Zifko et al., Injury, vol. 22, No. 1, 1991, pp. 60-62.

"Biomechanical substantiation of design features and physicomechanical characteristics of pins made of biocompatible polymers for intrasseous osteosynthesis" Davydov, Medical Progress through Technology, vol. 18, 1992, pp. 101-109.

"Locked Intramedullary Nailing of Humeral Shaft Fractures", Ingman et al., Journal of Bone and Joint Surgery, vol. 76, No. 1, 1994, pp. 23-29.

"Stress Analysis of a Partially Slotted Intramedullary Nail", Beaupre et al., Journal of Orthopaedic Research, vol. 2, No. 4, 1984, pp. 369-376.

Biomechanical Analysis of Supracondylar Femoral Fracturs Fixed with Modern Retrograde Intramedullary Nails, Hora et al., Journal of Orthopaedic Trauma, vol. 13, No. 8, 1999, pp. 539-544.

"Mechanical Characterization of a Totally Intramedullary Gradual Elongation Nail", Guichet et al., Clinical Orthopaedics and Related Resaerch, No. 337, 1997, pp. 281-290.

"Intramedullary nails: some design features of the distal end", C.J. Wang et al., Medical Engeneering Physics 25 (2003) pp. 789-794.

"Design of a retractable intramedullary nail for the humerus" Murdoch et al., Biomedical Materials and Enginnering, vol. 13, No. 3, 2003, pp. 297-307.

"Difficulty in Removal of a Femoral Intramedullary Nail: The Geometry of the Distal End of the Nail", Bombaci et al., Yonsei Medical Journal, vol. 44, No. 6, 2003, pp. 1083-1086.

"Development of Small Diameter Intrameduallary Nails Made from ISO 5832-9 Stainless Steel" Ingman, Australian and New Zealand Journal of Surgery, vol. 70, No. 3, 2000, pp. 221-225.

"Androdesis of the knee using a modular intramedullary nail" Walker et al., The Knee, vol. 5, No. 2, 1998, pp. 107-109—Walker.

"International Application Serial No. PCT/US2008/064680, International Preliminary Report on Patentability mailed Dec. 1, 2009", 6 pgs.

"International Application Serial No. PCT/US2008/064680, International Search Report mailed Aug. 22, 2008", 3 pgs.

"International Application Serial No. PCT/US2008/064680, Written Opinion Mailed Aug. 22, 2008", 5 pgs.

* cited by examiner

REINFORCED INTRAMEDULLARY NAIL

CROSS-REFERENCE TO RELATED APPLICATIONS

This application is a national phase filing of PCT International Application Serial No. PCT/US2008/064680, filed May 23, 2008, which claims the benefit under Title 35 U.S.C. §119(e) of U.S. Provisional Patent Application Ser. No. 60/931,783, entitled REINFORCED INTRAMEDULLARY NAIL, filed on May 25, 2007, the entire disclosures of which are expressly incorporated by reference herein.

BACKGROUND

1. Field of the Invention

The present invention relates to orthopedic components, and, particularly, to intramedullary nails.

2. Brief Description of the Related Art

Intramedullary nails may be used to align and stabilize fractures of a long bone. For example, in a fractured femur, an intramedullary nail may be inserted into the intramedullary canal of the femur and positioned to extend across the fracture line of the femur. Then, screws or other securement devices may be inserted within bores formed in the intramedullary nail to secure the opposing portions of the fractured femur together.

If the head of a long bone, such as the head of a femur, has fractured, lag screws may be inserted into transverse bores formed in an intramedullary nail to extend into the head of the long bone to compress the opposing portions of the fractured bone together. In this arrangement, the lag screw extends through a lag screw hole in the intramedullary nail and applies torque to the intramedullary nail. Because of the lag screw hole, the applied torque creates higher stress concentrations in the intramedullary nail near the lag screw hole.

United States Patent Application Publication No. US 2005/0149024 to Ferrante et al. describes an intramedullary nail that attempts to reduce stress in the intramedullary nail by increasing the size of a portion of the nail. As described in Ferrante et al., additional material is provided on a lateral side of the intramedullary nail. As shown in FIG. 1 of Ferrante et al., this additional material extends from a location distal of the lag screw hole to a proximal end of the intramedullary nail. During preparation of the femur to receive this intramedullary nail, a surgeon must remove additional bone along a substantial extent of the intramedullary canal to accommodate the additional material. Further, the surgeon must prepare a non-circular bore in the femur to receive the intramedullary nail of Ferrante et al.

SUMMARY

The present invention provides an intramedullary nail having a body with a transverse bore extending through the body. The transverse bore may be configured for receiving a lag screw or other securement device therein. The intramedullary nail also includes a strengthened area adjacent to the transverse bore. To strengthen the intramedullary nail in the areas around the transverse bore, additional material may be added to create an enlarged portion or area. By adding additional material to the areas around the transverse bore, the overall dimensions, e.g., the radius, of the body of the intramedullary rod may be lessened to preserve bone during preparation of the intramedullary canal of the long bone. The present invention also provides a surgical method for implanting an intramedullary nail having a strengthened area.

According to one aspect of the present invention, an intramedullary nail configured for receipt in a long bone is provided. The intramedullary nail comprises an elongated body having a transverse bore extending therethrough and configured to receive a transverse member extending from the transverse bore. The elongated body includes an enlarged portion positioned adjacent to the transverse bore.

According to another aspect of the present invention, an intramedullary nail is provided that is configured for receipt in a long bone. The intramedullary nail comprises an elongated body having a transverse bore extending therethrough and configured to receive a transverse member extending from the transverse bore. The elongated body includes a first segment extending from a distal extent of the transverse bore to a proximal extent of the transverse bore, a second segment immediately proximal to the transverse bore, and a third segment immediately distal to the transverse bore. The first segment includes a bulge positioned adjacent to the transverse bore.

According to another aspect of the present invention, an intramedullary nail is provided that is configured for receipt in a long bone. The intramedullary nail comprises an elongated body having a segment including a transverse bore extending therethrough and configured to receive a transverse member extending from the transverse bore. The elongated body includes means for reinforcing the segment.

According to another aspect of the present invention, a method of treating a long bone is provided. The method comprises the steps of implanting an intramedullary nail into a long bone. The intramedullary nail includes an elongated body having a transverse bore and an enlarged portion positioned adjacent to the transverse bore. The method further includes positioning a transverse member into the transverse bore.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. The exemplification set out herein illustrates at least one preferred embodiment of the invention, in one form, and such exemplification is not to be construed as limiting the scope of the invention in any manner.

DETAILED DESCRIPTION

Figure 1:
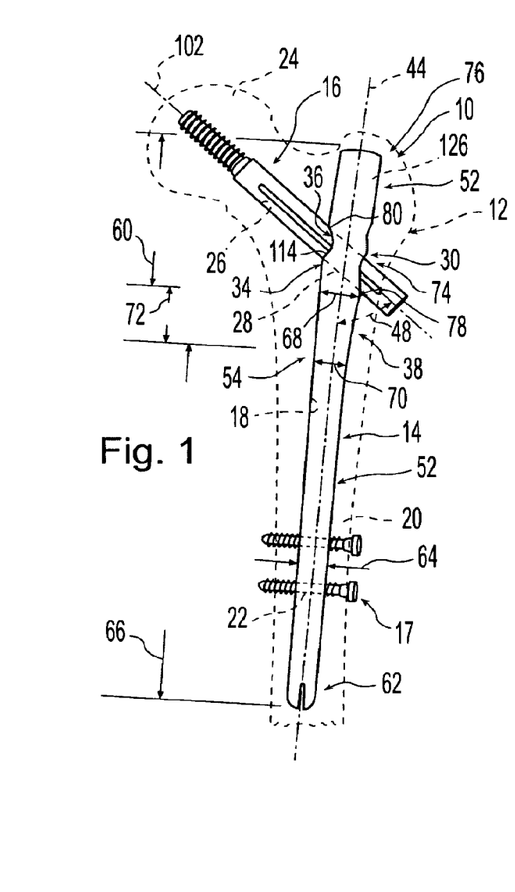
FIG. 1 is a view of a femur (in phantom) and an orthopedic assembly implanted in the femur showing the assembly including an intramedullary nail, a lag screw extending through the femoral head, and a pair of fixation screws extending through the femoral shaft.

Referring to FIG. 1, a view of orthopedic assembly 10 is shown implanted into femur 12. Orthopedic assembly 10 includes intramedullary nail 14, transverse member or lag screw 16, and fixation screws 17. During surgery, intramedullary nail 14 is implanted into prepared intramedullary canal 18. To prevent rotation and removal of intramedullary nail 14, fixation screws 17 are implanted into femoral shaft 20 through transverse bores 22 in intramedullary nail 14. In cases of a fracture or other trauma to femoral head 24, a surgeon implants lag screw 16 into prepared canal 26 and inserts lag screw 16 into transverse bore 28 of intramedullary nail 14. Intramedullary nail 14 may also be used in other long bones, such as the tibia, fibula, radius, ulna, clavicle, and other long bones.

During walking and other movement, some of the patients' weight is transferred to lag screw 16. As a result, lag screw 16 applies torque and force to intramedullary nail 14. Lag screw 16 applies a portion of this force to intramedullary nail 14 at locations 30 adjacent to lateral opening 32 and locations 34 adjacent to medial opening 36.

Figure 2:
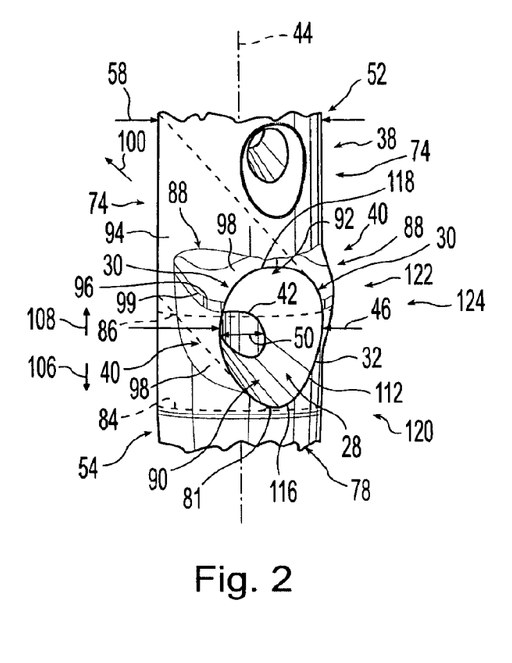
FIG. 2 is a fragmentary perspective view the intramedullary nail of FIG. 1 showing the intramedullary nail including an elongated body, a transverse bore for receiving the lag screw, and enlarged portions positioned adjacent to the transverse bore.
Figure 3:
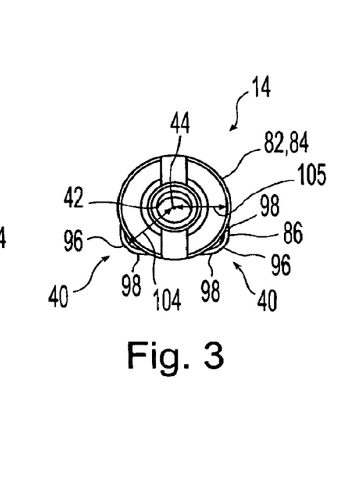
FIG. 3 is a top plan view of the intramedullary nail of FIG. 1.

To reinforce intramedullary nail 14 at location 30, elongated body 38 of intramedullary nail 14 includes reinforcing means 40 positioned at locations 30 as shown in FIG. 2. Reinforcing means 40 reduce the notch effect created by transverse bore 28. Reinforcing means 40 of FIG. 2 is discussed below in greater detail and is only one embodiment of the disclosed reinforcing means. FIGS. 6-13 also illustrate other reinforcing means that are discussed in greater detail below.

Intramedullary nail 14 is preferable made of a titanium alloy, such as Ti6Al4V, but may be made of other orthopedic materials. Intramedullary nail 14 includes elongated body 38 having transverse bore 28 and longitudinal bore 42 extending along longitudinal axis 44. According to the preferred embodiment, transverse bore 28 has diameter 46 of 10.5 mm (0.41 inches) at angle 48 (see FIG. 1) of 31-41° from longitudinal axis 44. Except for a proximal portion of longitudinal bore 42, diameter 50 of longitudinal bore 42 is 4.7 mm (0.19 inches).

Elongated body 38 includes proximal portion 52, intermediate portion 54, and distal portion 56. According to a preferred embodiment, proximal portion 52 is substantially cylindrical and has diameter 58 of 15 mm (0.59 inches) and length 60 of 55.6 mm (2.19 inches). Distal portion 56 is substantially cylindrical from intermediate portion 54 to tip portion 62 and has diameter 64 ranging from 10 mm (0.39 inches) to 14.5 mm (0.57 inches) depending on the patient anatomy and length 66 of 128.4 mm (5.06 inches). Intermediate portion 54 is substantially conical and transitions from diameter 68 of 15 mm (0.59 inches) to diameter 70 of 10 mm (0.39 inches) to 14.5 mm (0.57 inches) and length 72 of 31 mm (1.22 inches). Additional features of elongated body 38 are shown in greater detail in U.S. Provisional Patent Application Ser. No. 60/931,783, which is incorporated by reference herein.

As shown in FIG. 2, reinforcing means 40 is positioned in proximal portion 52 of elongated body 38 adjacent to lateral opening 32. Proximal portion 52 of elongated body 38 includes first or intermediate segment 74 through which transverse bore 28 extends, second or proximal segment 76 positioned proximal to intermediate segment 74, and third or distal segment 78 positioned distal to intermediate segment 74. Intermediate segment 74 extends from proximal extent 80 of transverse bore 28 to distal extent 81 of transverse bore 28. Proximal segment 76 and distal segment 78 have circular exterior profiles 82, 84 that are smaller than exterior profiles 86 of intermediate segment 74 that include reinforcement means 40 such that exterior profiles 82, 84 will fit within exterior profiles 86.

As shown in FIG. 2, reinforcing means 40 includes bulges or enlarged portions 88. According to one embodiment, reinforcing means 40 includes a single enlarged portion or bulge. Enlarged portions 88 are symmetric about lateral opening 32 and meet each other above lateral opening 32. Lateral opening 32 includes distal half 90 and proximal half 92 and a majority of enlarged portions 88 are positioned adjacent to proximal half 92 with a minority positioned adjacent to distal half 90.

Enlarged portions 88 extend radially outward from cylindrical portion 94 of elongated body 38 and include apex 96 and slopes 98 that extend radially inward toward cylindrical portion 94. Apex 96 is a portion of ridge 99 that extends from apex 96 to cylindrical portion 94 in direction 100 substantially parallel to longitudinal axis 102 of transverse bore 28. In a preferred embodiment, distance 104 from longitudinal axis 44 to a maximum radial extent of apex 96 is 8.8 mm (0.35 inches), whereas distance 105 from longitudinal axis 44 to a maximum radial extent of cylindrical portion 94 is 7.5 mm (0.30 inches). As a result, slopes 98 extend radially inwardly about 1.3 mm (0.06 inches). As shown in FIG. 2, slopes 98 also extend in distal and proximal longitudinal directions 106, 108 and in transverse direction 100.

Elongated body 38 includes first or lateral edge 112 that defines lateral opening 32 and medial or second edge 114 that defines medial opening 36. Lateral edge 112 includes distal-most portion 116 and proximal-most portion 118 positioned at first and second longitudinal positions 120, 122, respectively. Apex 96 is positioned at third longitudinal position 124 that is longitudinally positioned between first and second longitudinal positions 120, 122.

According to computer models, intramedullary nail 14 has lower stress concentrations and a higher safety margin than a similar larger intramedullary nail (not shown) without enlarged portions 88. In one specific computer-based example, intramedullary nail 14 was compared to an intramedullary nail without enlarged portions 88 and having diameter 58 of 16.5 mm (0.65 inches) in proximal portion 52. The maximum stress concentrations of intramedullary nail 14 near lateral opening 32 was about 25% lower and the safety margin was about 34% higher than the larger nail. Thus, smaller overall intramedullary nail 14 has lower stress concentrations and a higher safety factor than the larger overall intramedullary nail according to the computer models. In the computer models, the collodiaphyseal angle (CCD) was 125°.

According to one surgical technique, a surgeon reams, bores, or otherwise forms prepared intramedullary canal 18 in the cancellous bone tissue. Prepared intramedullary canal 18 is preferably circular in cross section and the same size or slightly larger than intramedullary nail 14, except for enlarged portions 88. For example, proximal portion 126 (see FIG. 1) of prepared intramedullary canal 18 is substantially cylindrical, but does not include a prepared recesses to receive enlarged portions 88. During implanting of intramedullary nail 14 into prepared intramedullary canal 18, enlarged portions 88 expand or push out the spongy cancellous bone tissue. After enlarged portions 88 pass the expanded cancellous bone tissue, the tissue collapses back to its prepared shape. As a result, portions of prepared intramedullary canal 18 proximal to implanted enlarged portions 88 have a diameter less than a width of intramedullary nail 14 at the location of enlarged portions 88. Because prepared intramedullary canal 18 can be smaller, less cancellous material needs to be removed and it is less likely that cortical bone will be removed during forming of prepared intramedullary canal 18.

Figure 4:
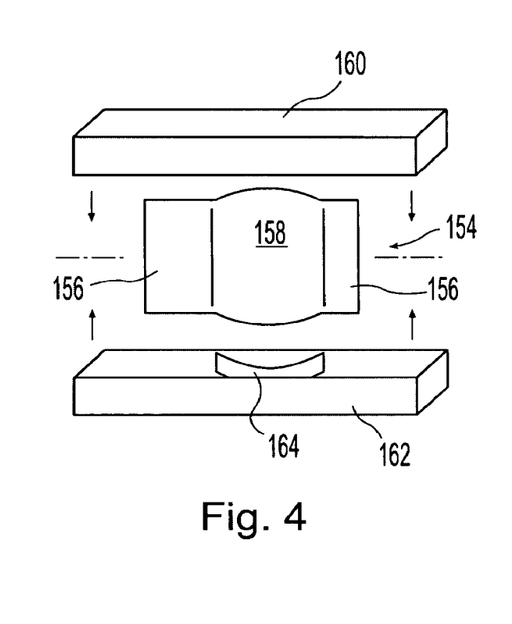
FIG. 4 is a view showing a pair of forging dies and an intramedullary nail blank positioned between the forging dies.
Figure 5:
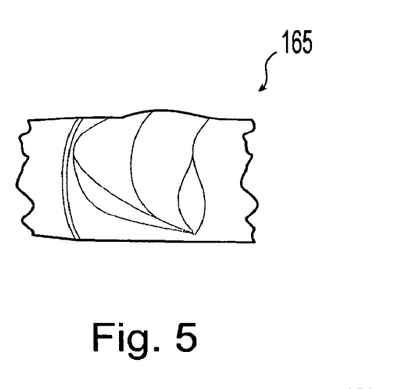
FIG. 5 is a fragmentary perspective view of the nail blank after being forged by the forging dies of FIG. 4.
Figure 6:
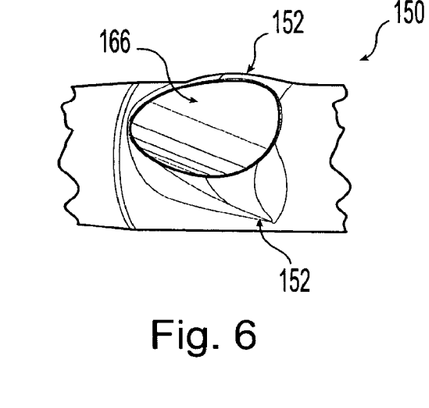
FIG. 6 is a fragmentary perspective view of the nail blank shown in FIG. 5 showing a transverse bore drilled into the forged nail blank.

FIGS. 4-6 illustrate a method of manufacturing intramedullary nail 150 with enlarged portions 152 that are similar to enlarged portions 88. Initially, nail blank 154 is provided that includes cylindrical portions 156 and bulb portion 158. Nail blank 154 is positioned between upper forging die 160 and lower forging die 162. Upper forging die 160 includes a recess (not shown) matching the cylindrical profile of cylindrical portions 156. Lower die 162 includes recess 164 that matches a desired contour of enlarged portions 152. After nail blank 154 is positioned between upper and lower forging dies 160, 162, upper and lower dies 160, 162 are brought together to forge nail blank 154, resulting in forged nail blank 165 shown in FIG. 5. Next, a drill (not shown) is used to drill out transverse bore 166.

According to another method, a Swiss lathe (not shown) is used to form enlarged portions 152 as shown in FIG. 5. After being turned on the lathe, a drill (not shown) is used to drill out transverse bore 166.

Figure 7:
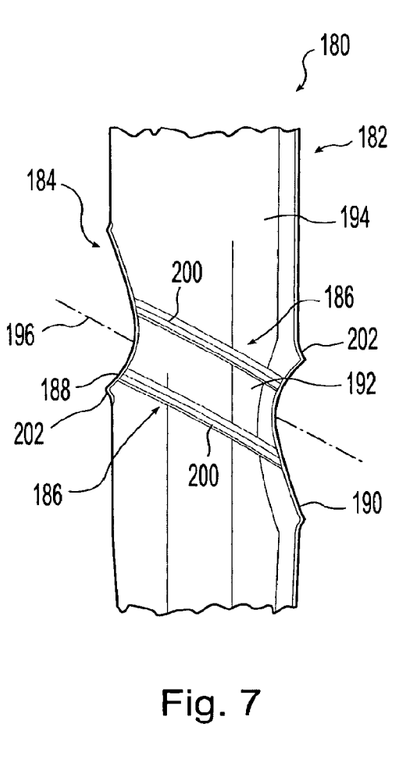
FIG. 7 is a fragmentary elevational view of an alternative embodiment intramedullary nail showing the intramedullary nail including an enlarged portion extending between lateral and medial openings of a lag screw transverse bore.
Figure 8:
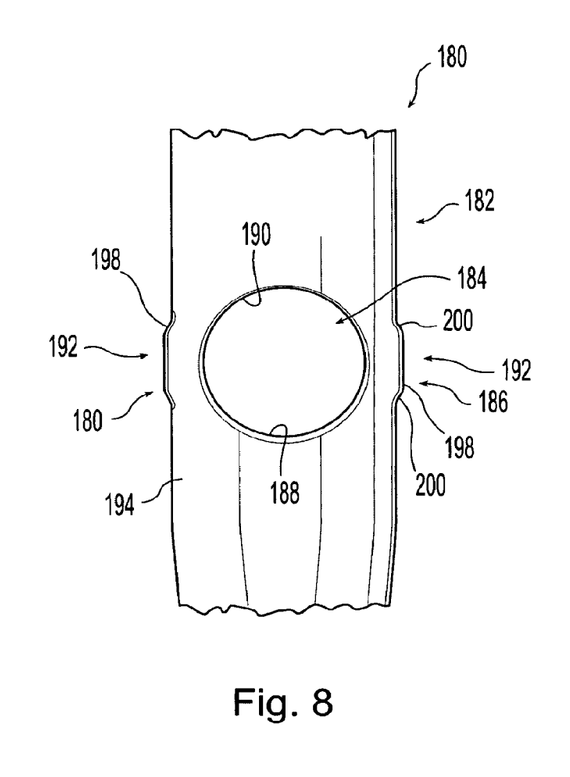
FIG. 8 is a fragmentary elevational view of the intramedullary nail of FIG. 7 along the transverse bore showing enlarged portions positioned on the anterior and posterior sides of the intramedullary nail.

An alternative embodiment intramedullary nail 180 is shown in FIGS. 7 and 8. Intramedullary nail 180 includes elongated body 182 having transverse bore 184 and reinforcing means 186 positioned adjacent to medial opening 188 and lateral opening 190. Reinforcing means 186 includes one or more elongated bulges or enlarged portions including ridges 192 that extending around substantially cylindrical portion 194 of elongated body 182. Ridges 192 extend parallel to longitudinal axis 196 of transverse bore 184. Ridges 192 include apexes 198 that extend along the substantial length of ridges 192 and slopes 200 that extends longitudinally and radially inward. Intramedullary nail 180 further includes raised lips 202 surrounding medial opening 188 and lateral opening 190. Other features of intramedullary nail 180 are the same as or similar to intramedullary nail 14 discussed above.

Figure 9:
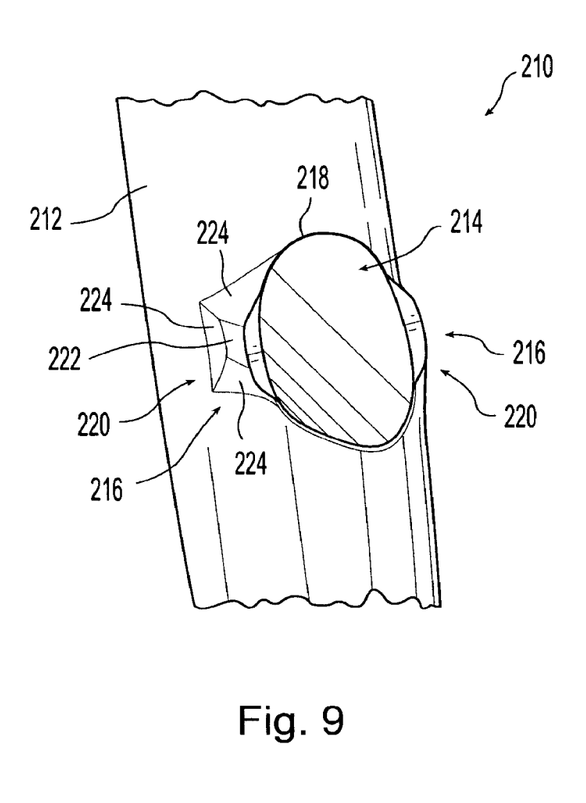
FIG. 9 is a fragmentary perspective view of an alternative embodiment intramedullary nail showing the intramedullary nail including an enlarged portion positioned adjacent to a lateral opening of a lag screw transverse bore and including a cut out.
Figure 10:
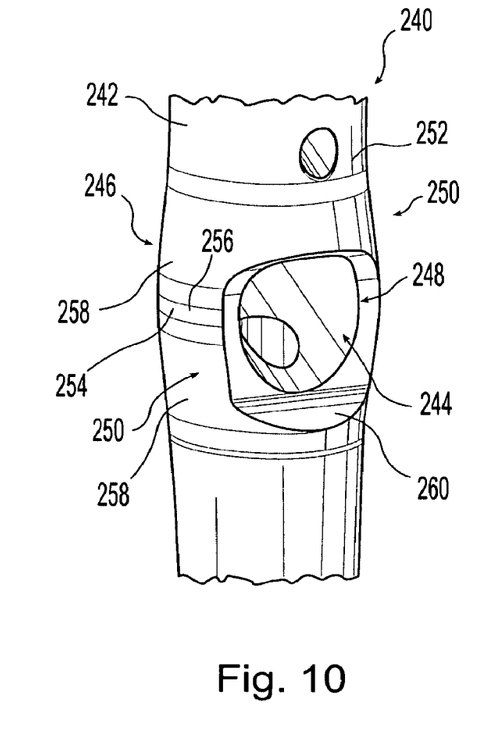
FIG. 10 is a fragmentary elevational view of an alternative embodiment intramedullary nail showing the intramedullary nail including enlarged portions extending around the circumference of the intramedullary nail adjacent to a lateral opening of a lag screw transverse bore and including a cut out.

Another alternative embodiment intramedullary nail 210 is shown in FIG. 9. Intramedullary nail 210 includes elongated body 212 having transverse bore 214 and reinforcing means 216 positioned adjacent to lateral opening 218. Reinforcing means 216 includes one or more bulges or enlarged portions 220 having substantially flat apexes 222 and slopes 224 that extends longitudinally and radially inward. Intramedullary nail 210 may further include a small cut out around lateral opening 218. A larger such cut out is shown in FIG. 10 as described below. Other features of intramedullary nail 210 are the same as or similar to intramedullary nail 14 discussed above.

Another alternative embodiment intramedullary nail 240 is shown in FIG. 10. Intramedullary nail 240 includes elongated body 242 having transverse bore 244 and reinforcing means 246 positioned adjacent to lateral opening 248. Reinforcing means 246 includes one or more bulges or enlarged portions 250 that extend around substantially cylindrical portion 252 of elongated body 242. Enlarged portions 250 include ridges 254 that extend circumferentially. Ridges 254 include apexes 256 that extend along the substantial length of ridges 254 and slopes 258 that extends longitudinally and radially inward. Intramedullary nail 210 further includes cut out 260 that surrounds lateral opening 248. Other features of intramedullary nail 240 are the same as or similar to intramedullary nail 14 discussed above.

Figure 11:
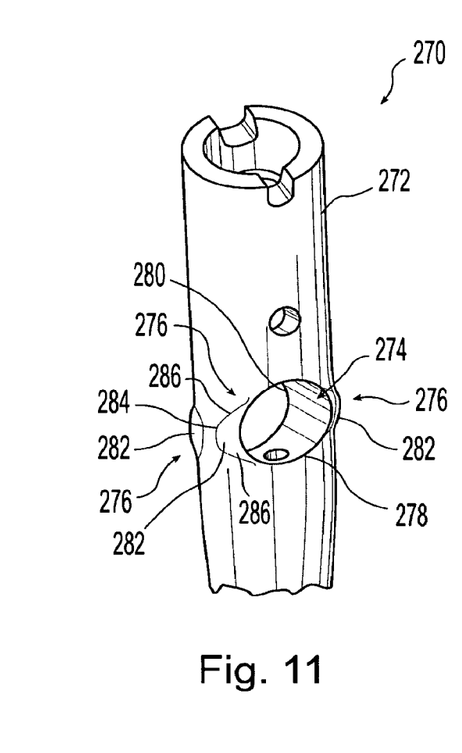
FIG. 11 is a fragmentary perspective view of an alternative embodiment intramedullary nail showing the nail including an elongated body and a pair of enlarged portions positioned adjacent to a medial opening to a lag screw transverse bore and an enlarged portion positioned adjacent a lateral opening to the lag screw transverse bore.

Another alternative embodiment intramedullary nail 270 is shown in FIG. 11. Intramedullary nail 270 includes elongated body 272 having transverse bore 274 and reinforcing means 276 positioned adjacent to medial opening 278 and lateral opening 280. Reinforcing means 276 includes four bulges or enlarged portions 282. Enlarged portions 282 include apexes 284 and slopes 286. Some of slopes 286 extends longitudinally and radially inward. Other slopes 286 extending transversely and radially inward. Other features of intramedullary nail 270 are the same as or similar to intramedullary nail 14 discussed above.

Figure 12:
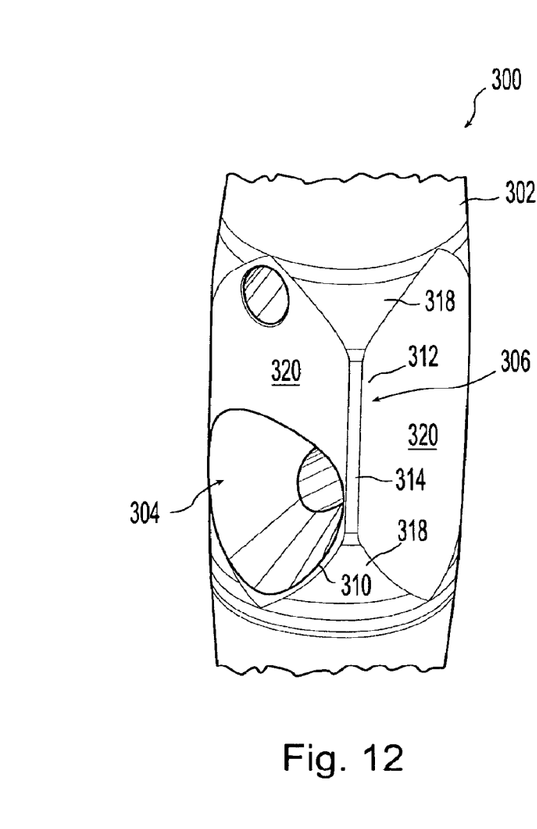
FIG. 12 is a fragmentary perspective view of an alternative embodiment intramedullary nail showing the intramedullary nail including an elongated body and an enlarged portion positioned adjacent to a lateral opening to a lag screw transverse bore.
Figure 13:
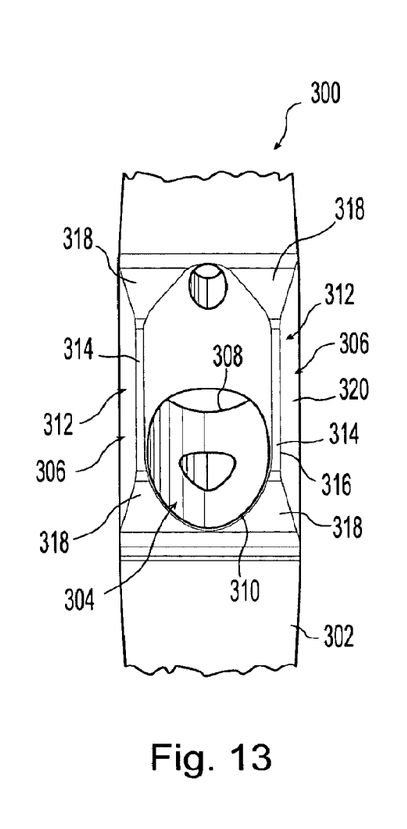
FIG. 13 is a fragmentary elevational view of the intramedullary nail of FIG. 12 showing another enlarged portion positioned adjacent to the lateral opening.
Figure 14:
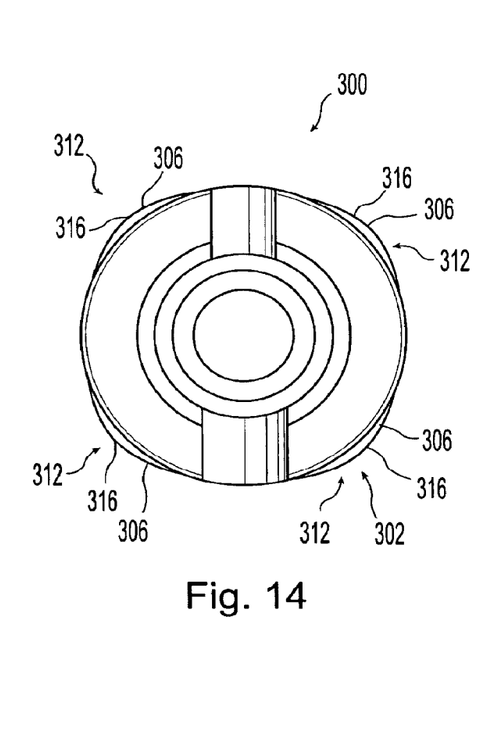
FIG. 14 is a top plan view of the intramedullary nail of FIG. 12.

Another alternative embodiment intramedullary nail 300 is shown in FIGS. 12-14. Intramedullary nail 300 includes elongated body 302 having transverse bore 304 and reinforcing means 306 positioned adjacent to medial opening 308 and lateral opening 310. Reinforcing means 306 includes four bulges or enlarged portions 312. Enlarged portions 312 include longitudinally extending ridges 314 having apexes 316 and slopes 318, 320. Slopes 318 extends longitudinally and radially inward. Slopes 320 extending transversely and radially inward. Other features of intramedullary nail 300 are the same as or similar to intramedullary nail 14 discussed above.

Figure 15:
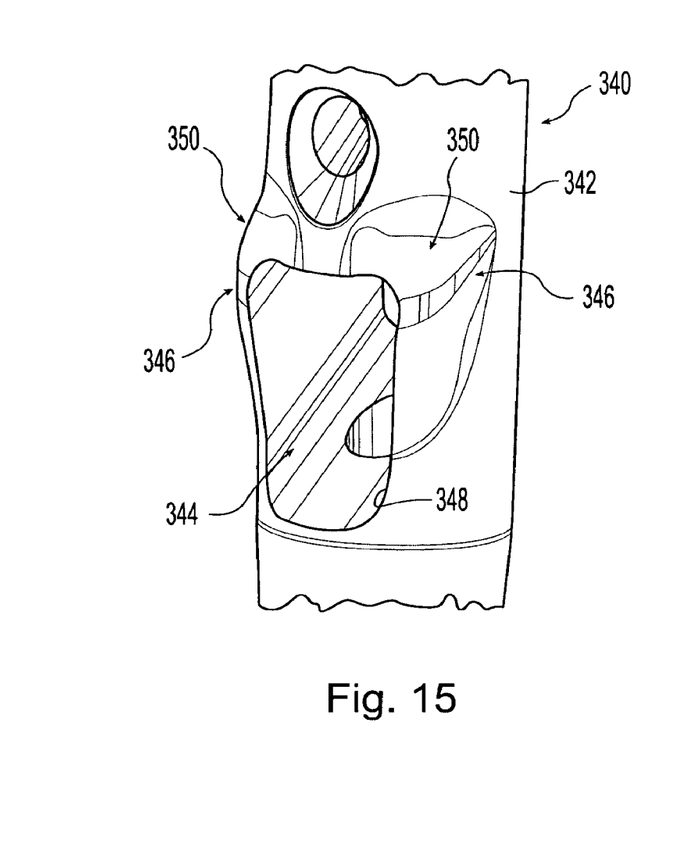
FIG. 15 is a fragmentary perspective view an alternative embodiment intramedullary nail showing a trapezoidal lag screw transverse bore and a pair of enlarged portions positioned adjacent to proximal corners of the transverse bore.

Another alternative embodiment intramedullary nail 340 is shown in FIG. 15. Intramedullary nail 340 includes elongated body 342 having trapezoidal transverse bore 344 sized to receive a lag screw (not shown) having a trapezoidal cross section. Elongated body 342 further includes reinforcing means 346 positioned adjacent to lateral opening 348. Reinforcing means 346 includes bulges or enlarged portions 350 substantially similar to enlarged portions 88 shown in FIG. 2. Other features of intramedullary nail 340 are the same as or similar to intramedullary nail 14 discussed above.

Figure 16:
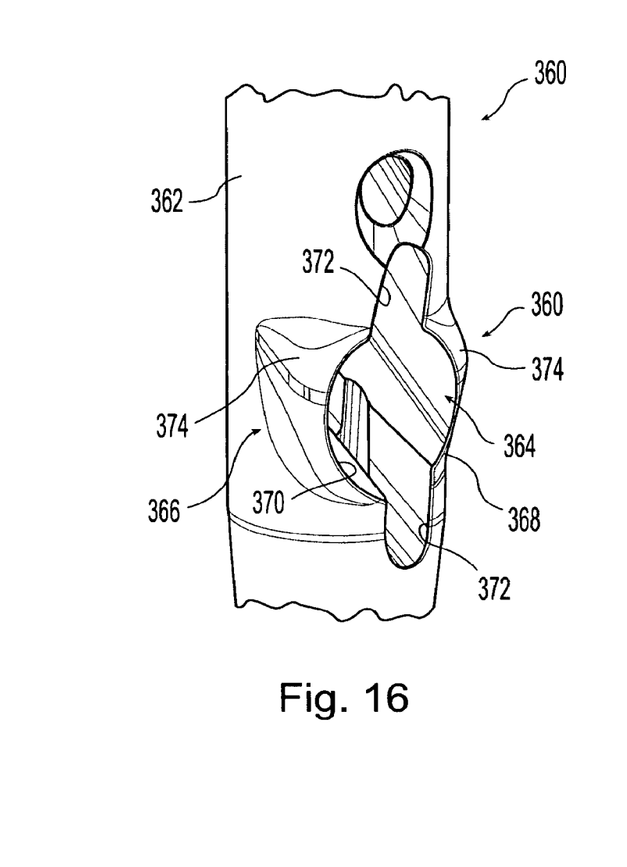
FIG. 16 is a fragmentary perspective view of an alternative embodiment intramedullary nail showing a lag screw transverse bore having a cylindrical portion and two slots and a pair of enlarged portions positioned adjacent to the transverse bore.

Another alternative embodiment intramedullary nail 360 is shown in FIG. 16. Intramedullary nail 360 includes elongated body 362 having transverse bore 364 and reinforcing means 366 positioned adjacent to lateral opening 368. Transverse bore 364 includes substantially cylindrical portion 370 and slots 372. Reinforcing means 366 includes bulges or enlarged portions 374 substantially similar to enlarged portions 88 shown in FIG. 2. Other features of intramedullary nail 340 are the same as or similar to intramedullary nail 14 discussed above.

Intramedullary nail 14 may also be configured and utilized in accordance with the teachings of U.S. Pat. No. 5,034,013, entitled INTRAMEDULLARY NAIL, issued Jul. 23, 1991; U.S. Pat. No. 5,122,141, entitled MODULAR INTRAMEDULLARY NAIL, issued Jun. 16, 1992; U.S. Pat. No. 5,645,545, entitled SELF-REAMING INTRAMEDULLARY NAIL AND METHOD OF USING THE SAME, issued Jul. 8, 1997; U.S. Pat. No. 4,275,717, entitled INTRAMEDULLARY FIXATION DEVICE FOR FRACTURED TUBULAR BONES, issued Jun. 30, 1981; U.S. Pat. No. 4,781,181, entitled BORE SENSOR FOR INTRAMEDULLARY NAIL AND CORRESPONDING INTRAMEDULLARY NAIL, issued Nov. 1, 1988; U.S. Pat. No. 4,969,889, entitled INSTRUMENT FOR LOCATING A HOLE, issued Nov. 13, 1990; U.S. Pat. No. 7,144,399, entitled INSTRUMENTATION GUIDE FOR ORTHOPEDIC SURGERY, issued Dec. 5, 2006; and U.S. patent application Ser. No. 10/682,745, entitled BONE FIXING SYSTEM, filed Oct. 9, 2003, the entire disclosures of which are hereby expressly incorporated by reference herein. Further, intramedullary nail 14 may also be configured and utilized in accordance with the teachings of the surgical techniques and product descriptions set forth in attached Exhibit B, i.e., Zimmer® ITST™ Intertrochanteric/Subtrochanteric Fixation IM Nail System; Zimmer® ITST™ Intertrochanteric/Subtrochanteric Fixation IM Nail System; M/DN® Intramedullary Fixation; M/DN® Femoral Interlocking & Recon Nail Intramedullary Fixation Surgical Technique; M/DN® Femoral Retrograde Intramedullary Fixation Surgical Technique; M/DN® MIS™ Intramedullary Femoral Fixation Surgical Technique; M/DN® Tibial and Humeral Intramedullary Fixation Surgical Technique; M/DN® Tibial Intramedullary Nail Utilizing the MIS™ Tibial Guide Surgical Technique; Zimmer Sirus® Intramedullary Nail System; Sirus® Intramedullary Femur Nail System Surgical Technique; and Sirus® Intramedullary Tibia Nail System Surgical Technique, copies of which are provided in U.S. Patent Application Ser. No. 60/931,783, which is hereby expressly incorporated by reference herein.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An intramedullary nail configured for receipt in a long bone, comprising:

an elongated body having a lateral side, a medial side, and a transverse bore extending therethrough having a longitudinal axis, the transverse bore configured to receive a transverse member extending from the transverse bore, wherein the elongated body includes a first segment extending from a distal extent of the transverse bore to a proximal extent of the transverse bore, a second segment immediately proximal to the transverse bore, and a third segment immediately distal to the transverse bore, wherein the lateral side of the elongated body of the first segment includes a bulge positioned adjacent to the transverse bore creating a maximum external profile of the first segment at a first location, positioned along the lateral side of the elongated body, that is greater than at least one of a maximum external profile of the second segment and a maximum external profile of the third segment, the bulge including a ridge extending substantially parallel to the longitudinal axis, the ridge including an apex and a slope that extends radially inward, wherein the medial side of the first segment of the elongated body lacking a bulge positioned adjacent to the transverse bore creating a minimum external profile of the first segment at a second location, positioned along the medial side of the elongated body, that is the same as at least one of the maximum external profile of the second segment and the maximum external profile of the third segment, and wherein the maximum external profile of the first segment is greater than the minimum external profile of the first segment, and wherein the first location and the second location are positioned on a plane perpendicular to a longitudinal axis of the first segment of the elongated body.

2. The intramedullary nail of claim 1, wherein the second and third segments are substantially cylindrical.

3. The intramedullary nail of claim 1, wherein the first segment includes a longitudinal axis and a plane included in the longitudinal axis that divides the first segment into a medial portion and a lateral portion, and the bulge extends to the plane.

4. An intramedullary nail configured for receipt in a long bone, comprising:

a transverse member; and an elongated body having a longitudinal axis and a transverse bore extending therethrough and configured to receive the transverse member extending from the transverse bore, the transverse member having sufficient length to extend beyond the elongated body and into the bone, wherein the elongated body includes a first segment extending from a distal extent of the transverse bore to a proximal extent of the transverse bore and including an enlarged portion, a second segment immediately proximal to the transverse bore, and a third segment immediately distal to the transverse bore, the enlarged portion defined by a surface of the elongated body and creates a non-uniform exterior profile along a longitudinal length of the first segment, wherein the enlarged portion includes a first radial-most extent at a first location along the longitudinal length, a second radial-most extent at a second location along the longitudinal length, and a third radial-most extent at a third location along the longitudinal length, the first, second, and third locations being longitudinally spaced apart, the second radial-most extent being positioned further away from the longitudinal axis than at least one of the first and third longitudinal extents and the second radial-most extent being positioned between the first and third location, and wherein the enlarged portion includes at least one of a proximal-most extent that terminates distally of the proximal-most extent of the transverse bore and a distal-most extend that terminates proximally of the distal-most extent of the transverse bore.

5. The intramedullary nail of claim 4, wherein the exterior profiles of the second and third segments are substantially circular immediately adjacent the transverse bore.

6. The intramedullary nail of claim 4, wherein the elongated body includes another enlarged portion positioned adjacent to the transverse bore.

7. The intramedullary nail of claim 4, wherein the enlarged portion includes the proximal-most extent that terminates distally of the proximal-most extent of the transverse bore and the distal-most extent that terminates proximally of the distal-most extent of the transverse bore.

8. An intramedullary nail configured for receipt in a long bone, comprising:
an elongated body having a longitudinal axis, a medial side, a lateral side, and a transverse bore extending from the lateral side to the medial side and configured to receive a transverse member, the elongated body having a first segment extending from a distal extent of the transverse bore to a proximal extent of the transverse bore and including an enlarged portion positioned adjacent to the transverse bore, wherein the enlarged portion includes at least one of a proximal-most extent that terminates distally of the proximal-most extent of the transverse bore and a distal-most extend that terminates proximally of the distal-most extent of the transverse bore, wherein the medial side of the first segment of the elongated body has a maximum medial extent measured medially from the longitudinal axis along a plane perpendicular to the longitudinal axis and the lateral side of the first segment of the elongated body having a maximum lateral extent measured laterally from the longitudinal axis along the plane perpendicular to the longitudinal axis, the maximum lateral extent differing from the maximum medial extent, wherein the traverse bore has a longitudinal axis and the enlarged portion includes a ridge extending substantially parallel to the longitudinal axis of the transverse bore, the ridge including an apex and a slope that extends radially inward.

9. The intramedullary nail of claim 8, wherein the elongated body includes a second segment immediately proximal to the transverse bore, and a third segment immediately distal to the transverse bore, the first segment has an exterior profile larger than the exterior profiles of the second and third segments.

10. The intramedullary nail of claim 9, wherein the exterior profiles of the second and third segments are substantially circular.

11. The intramedullary nail of claim 8, wherein the elongated body includes an opening to the transverse bore, the opening has a distal half and a proximal half, and the enlarged portion is positioned adjacent to the proximal half.

12. The intramedullary nail of claim 8, wherein the elongated body includes a substantially cylindrical portion and the enlarged portion is positioned adjacent to the substantially cylindrical portion.

13. The intramedullary nail of claim 8, wherein the apex and the slope extend in a longitudinal and radially inward direction relative to the longitudinal axis of the elongated body.

14. The intramedullary nail of claim 8, wherein the enlarged portion is located on the lateral side of the first segment of the elongated body, the maximum lateral extent exceeding the maximum medial extent.

15. An intramedullary nail configured for receipt in a long bone, comprising:
an elongated body having a longitudinal axis, a medial side, a lateral side, and a transverse bore extending from the lateral side to the medial side and configured to receive a transverse member, the elongated body having a first segment extending from a distal extent of the transverse bore to a proximal extent of the transverse bore and including an enlarged portion positioned adjacent to the transverse bore, wherein the enlarged portion includes at least one of a proximal-most extent that terminates distally of the proximal-most extent of the transverse bore and a distal-most extend that terminates proximally of the distal-most extent of the transverse bore, wherein the medial side and the lateral side of the elongated body at the first segment are asymmetrically arranged relative to the longitudinal axis, wherein the enlarged portion is located on the lateral side of the first segment of the elongated body, the lateral side of the first segment of the elongated body having a non-circular outer periphery along a plane perpendicular to the longitudinal axis, and the medial side of the first segment of the elongated body having a circular outer periphery along the plane perpendicular to the longitudinal axis, and wherein the transverse bore has a longitudinal axis and the enlarged portion includes a ridge extending substantially parallel to the longitudinal axis of the transverse bore, the ridge including an apex and a slope that extends radially inward.

16. The intramedullary nail of claim 15, wherein the elongated body includes a first edge defining a lateral opening into the transverse bore and a second edge defining a medial opening into the transverse bore, the first edge includes a distal-most portion positioned at a first longitudinal position and a proximal-most portion positioned at a second longitudinal position, and the apex is positioned longitudinally between the first longitudinal position and the second longitudinal position.

* * * * *